United States Patent [19]
Cavalla et al.

[11] Patent Number: 5,591,776
[45] Date of Patent: Jan. 7, 1997

[54] PHEYNL OR BENZYL-SUBSTITUTED ROLIPRAM-BASED COMPOUNDS FOR AND METHOD OF INHIBITING PHOSPHODIESTERASE IV

[75] Inventors: David J. Cavalla, Cambridge, England; Lloyd J. Dolby, Eugene, Oreg.; Mark Chasin, Manalapan, N.J.

[73] Assignee: Euro-Celtique, S.A., Luxembourg, Luxembourg

[21] Appl. No.: 370,952

[22] Filed: Jan. 10, 1995

Related U.S. Application Data

[63] Continuation-in-part of Ser. No. 265,641, Jun. 24, 1994.
[51] Int. Cl.$^6$ ...................... A61K 31/165; C07C 233/08
[52] U.S. Cl. .................. 514/622; 564/174; 564/177
[58] Field of Search ........................ 514/622; 564/174, 564/177

[56] References Cited

U.S. PATENT DOCUMENTS

| | | | |
|---|---|---|---|
| 3,135,753 | 6/1964 | Hitchings | 544/276 |
| 4,925,847 | 5/1990 | Hofer | 544/276 |

FOREIGN PATENT DOCUMENTS

| | | | |
|---|---|---|---|
| 0178413 | 4/1986 | European Pat. Off. | C07D 235/18 |
| 0470805 | 2/1992 | European Pat. Off. | C07C 271/60 |
| 0497564 | 8/1992 | European Pat. Off. | C07C 235/36 |
| 0511865 | 11/1992 | European Pat. Off. | C07D 231/08 |
| 1548252 | 12/1968 | France . | |
| 1077689 | 8/1967 | United Kingdom . | |
| 1498705 | 1/1978 | United Kingdom | A61K 31/40 |
| 2041359 | 9/1980 | United Kingdom . | |
| WO9219594 | 11/1992 | WIPO | C07D 207/26 |
| WO9307111 | 4/1993 | WIPO | C07C 49/753 |
| WO9314082 | 7/1993 | WIPO | C07D 401/04 |
| WO9315044 | 8/1993 | WIPO | C07C 237/22 |
| WO9315045 | 8/1993 | WIPO | C07C 237/22 |
| WO9319747 | 10/1993 | WIPO | A61K 31/275 |
| WO9325517 | 12/1993 | WIPO | C07C 233/75 |
| WO9402465 | 2/1994 | WIPO | C07D 213/75 |
| WO9410118 | 5/1994 | WIPO | C07C 431/235 |
| WO9412461 | 6/1994 | WIPO | C07C 65/21 |
| WO9414800 | 7/1994 | WIPO | C07D 405/06 |
| WO9414742 | 7/1994 | WIPO | C07C 43/253 |
| WO9420455 | 9/1994 | WIPO | C07C 255/36 |
| WO9420446 | 9/1994 | WIPO | C07C 43/235 |

OTHER PUBLICATIONS

CA116:255335, 1992.
CA114:246982, 1990.
CA103:37354, 1985.
CA92:6207, 1977.
CA88:51054, 1977.
Chem. Abstracts, vol. 82 (19), May 12, 1975, Abstract #49027b.
Chem. Abstracts, vol. 75 (7), Aug. 16, 1971, Abstract #125358x.
Tetrahedron Letters, vol. 23 (No. 21), 1982, pp. 2203–2204.
Chem. Abstracts, vol. 85 (1) Jul. 5, 1976, Abstract #5692S.
Chem. Abstracts. vol. 84 (25) Jun. 21, 1976, Abstract #180,299v.
Chem. Abstracts. vol. 86 (7) Feb. 14, 1977, Abstract #43, 746r.
"Could Isoenzyme–selective phosphodiesterase Inhibitiors render bronchodilator therapy, redundant in the treatment of bronchial asthma?". Mark A. Glembycz, Biochemical Pharmacology. 1992, vol. 43. No. 10, pp. 2041–2051.

(List continued on next page.)

*Primary Examiner*—Yogendra N. Gupta
*Attorney, Agent, or Firm*—Steinberg, Raskin & Davidson, P.C.

[57] ABSTRACT

Rolipram-based PDE IV inhibitors containing phenyl- or benzyl-substituted moieties of the formula:

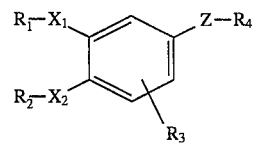

wherein $X_1$ and $X_2$ may be the same or different and each is O or S;

$R_1$ is selected from the group consisting of hydrogen, saturated or unsaturated straight-chain or branched $C_{2-12}$ alkyl groups, cycloalkyl and cycloalkyl-alkyl groups containing from 3 to 10 carbon atoms in the cycloalkyl moiety;

$R_2 = R_1$ or $-CH_3$;

$R_3$ is hydrogen, halogen, or a saturated or unsaturated straight-chain or branched $C_{1-12}$ alkyl group, a cycloalkyl or cycloalkyl-alkyl groups containing from 3 to 7 carbon atoms in the cycloalkyl moiety;

Z is a linkage selected from $-CH_2CONH-$ or $-CH_2NHCO-$, and $R_4$ is a phenyl or benzyl which may be unsubstituted or substituted with one or more halogen atoms, alkyl groups, hydroxyl groups, cyano groups, carboxyl groups, alkoxy groups, alkoxycarbonyl, amido, carboxamido, substituted or unsubstituted amino groups, cycloalkyl and cycloalkyl-alkyl groups containing from 3 to 10 carbon atoms in the cycloalkyl moiety, aryl or aralkyl groups preferably containing from about 6 to about 10 carbon atoms, or heterocyclic groups containing nitrogen, oxygen or sulfur in the ring; the alkyl, alkoxy, cycloalkyl, cycloalkylalkyl, aryl, and aryl-alkyl groups being saturated or unsaturated, unsubstituted or substituted by halogen atoms, hydroxy groups, cyano groups, carboxyl groups, alkoxy groups, alkoxycarbonyl, carboxamido or substituted or unsubstituted amino groups, or one or more lower alkyl groups having from 1 to 3 carbon atoms;

provided that $R_4$ cannot be substituted with more than one methoxy group. compared to theophylline or rolipram as well as with improved selectivity with regard to PDE III inhibition. Pharmaceutical compositions containing the same and methods of treatment are also disclosed.

15 Claims, No Drawings

OTHER PUBLICATIONS

"Differential pharmacologic sensitivity of cyclic nucleotide phosphodiesterase isozymes isolated from cardiac muscle, arterial and airway smooth muscle", Paul J. Silver, Linda T. Hamel, Mark II, Perrone, Ross G. Bently, Cynthia R. Bushover and Dale B. Evans, European Journal of Phamacology, 150 )1988) 85–94, Elsvier.

"The pharmacology and therapeutic use of theophylline", Miles Weinberger, M. D., The Journal of Allergy and Clincial Immamology, vol. 73, No. 5, Part 1, 525–544.

"Assay of cyclic nucleotide phosphodiesterase and resolution of multiple molecular forms of the enzyme", W. Joseph Thompson, Wesley L. Terasaki, Paul M. Epstein, Samuel J. Strada, Advances in Cyclic Nucleotide Research, vol. 10, 1979, 69–92.

"Identification, characterization and functional role of phosphodiesterase isozymes in lamen airway smooth muscle", Theodore J. Torphy, Bradley J. Undem. Lenora B. Cleslinski, Mark A. Luttmann, Martin L. Reeves and Douglas W. P. Llay, The Journal of Pharmacology and Experimental Therapeutics, 1993, vol. 265, No. 3, 1213–1223.

"The PDE IV family of calcium–independent phosphodiesterase enzymes", John A. Lowe III and John B. Cheng, Drugs of the Future 1992, 17(9): 799–807.

"Differential modulation of tissue function and therapeutic potential of selective inhibitors of cyclic nucleotide phosphodiesterase isoenzymes", C. David Nicholson, R. A. John Ciulliss and Mohammed Shahid, 1991, Elsevier Science Publishers Ltd. (UK), TIPS 12:19–27.

"Phosphodlisterase inhibitors: new opportunities for the treatment of asthma", Theodore J. Torphy, Bradley J. Undem. Thorax 1991: 46:512–523.

"Novel phosphodiesterase inhibitors for the therapy of asthma", Theodore J. Torphy, George P. Livi and Siegfried B. Christensen, DN&P 6(4), May 1993 203–214.

PHEYNL OR BENZYL-SUBSTITUTED ROLIPRAM-BASED COMPOUNDS FOR AND METHOD OF INHIBITING PHOSPHODIESTERASE IV

This application is a continuation-in-part of U.S. patent application Ser. No. 08/265,641 filed Jun. 24, 1994.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these actually may contribute to its activity, only PDE inhibition may account for both the anti-inflammatory and bronchodilatory components. However, theophylline is known to have a narrow therapeutic index, and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al , "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, anti-inflammatory and ant-depressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula:

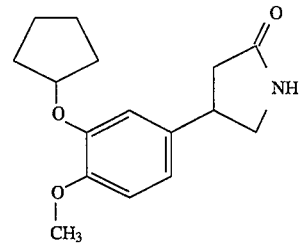

and of RO-20-1724, which has the following structural formula:

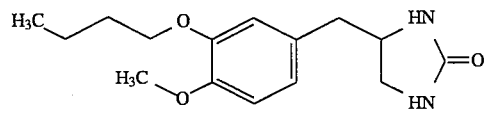

have been studied.

Rolipram, which was initially studied because of its activity as an antidepressant has been shown to selectively inhibit the PDE IV enzyme and this compound has since become a standard agent in the classification of PDE enzyme subtypes. There appears to be considerable therapeutic potential for PDE IV inhibitors. Besides initial work suggesting an anti-depressive action, rolipram has been investigated for its anti-inflammatory effects, particularly in asthma. In-vitro, rolipram, RO20-1724 and other PDE IV inhibitors have been shown to inhibit (1) mediator synthesis/ release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down-regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a nonselective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and anti-inflammatory properties would be most advantageous.

It appears that selective PDE IV inhibitors should be more effective with fewer side effects than theophylline.

Attempts have therefore been made to find new compounds having more selective and improved PDE IV inhibition.

OBJECTS AND SUMMARY OF THE INVENTION

It is accordingly a primary object of the present invention to provide new compounds which are effective PDE IV inhibitors.

It is another object of the present invention to provide new compounds which act as effective PDE IV inhibitors with lower PDE III inhibition.

It is a further object of the present invention to provide new compounds which have a superior PDE IV inhibitory effect as compared to theophylline or other known compounds.

It is a further object of the present invention to provide new compounds which have a substantially equal or superior PDE IV inhibitory effect as compared to known chemical compounds, and which exhibit surprisingly greater selectivity with regard to their inhibitory effects.

It is another object of the present invention to provide a method of treating a patient requiring PDE IV inhibition.

It is another object of the present invention to provide new compounds for treating disease states associated with abnormally high physiological levels of cytokines, including tumor necrosis factor.

It is another object of the present invention to provide a method of synthesizing the new compounds of this invention.

It is another object of the present invention to provide a method for treating a mammal suffering from a disease state selected from the group consisting of asthma, arthritis, allergies, inflammation, depression, dementia and disease states associated with abnormally high physiological levels of cytokines.

With the above and other objects in view, the present invention mainly comprises a compound of the formula:

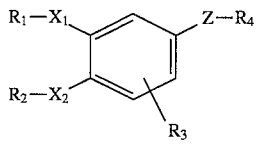

wherein:

$X_1$ and $X_2$ may be the same or different and each is O or S;

$R_1$ and $R_2$ may be the same or different and each is selected from the group consisting of hydrogen, saturated or unsaturated straight-chain or branched $C_{1-12}$ alkyl groups, cycloalkyl and cycloalkyl-alkyl groups containing from 3 to 10 carbon atoms in the cycloalkyl moiety;

$R_3$ is hydrogen, halogen, or a saturated or unsaturated straight-chain or branched $C_{1-12}$ alkyl group, a cycloalkyl and cycloalkyl-alkyl groups containing from 3 to 7 carbon atoms in the cycloalkyl moiety;

Z is a linkage selected from $-NHCH_2-$, $-CH_2NH-$, $-CH_2CONH-$, $-CH_2NHCO-$, $-CH_2CO-$, $-COCH_2-$, $-CH_2COCH_2-$, $-C(=NQ)NH-$ and $C(=NOCONHQ)-$;

$R_4$ is a phenyl or benzyl or a 6-membered heteroaryl group which may be unsubstituted or substituted with one or more halogen atoms, alkyl groups, hydroxyl groups, cyano groups, nitro groups, carboxyl groups, alkoxy groups, alkoxycarbonyl, amido, carboxamido, substituted or unsubstituted amino groups, cycloalkyl and cycloalkyl-alkyl groups containing from 3 to 10 carbon atoms in the cycloalkyl moiety, aryl or aralkyl groups preferably containing from about 6 to about 10 carbon atoms, or heterocyclic groups containing nitrogen, oxygen or sulfur in the ring; said alkyl, cycloalkyl, cycloalkyl-alkyl, aryl, and aryl-alkyl groups being unsubstituted or substituted by halogen atoms, hydroxyl groups, cyano groups, carboxyl groups, alkoxy groups, alkoxycarbonyl, carboxamido or substituted or unsubstituted amino groups, or one or more lower alkyl groups having from 1 to 3 carbon atoms;

Q is $R_4$ or hydrogen;

except that when $Z=-C(=NOCONHQ)-$, $R_4$ is not benzyl; and $R_1$ and $R_2$ are both not hydrogen.

The term "lower alkyl" is defined for purposes of the present invention as straight or branched chain radicals having from 1 to 3 carbon atoms.

DETAILED DESCRIPTION

The compounds of the present invention, as demonstrated in the appended examples, are effective in the mediation or inhibition of PDE IV in humans and other mammals. Further, these compounds are selective PDE IV inhibitors which possess both bronchodilatory and anti-inflammatory properties substantially without undesirable cardiovascular stimulation caused by PDE III inhibition. Many of these compounds have a substantially equal or superior PDE IV inhibitory effect as compared to theophylline.

The present invention is further related to a method for the treatment of allergic and inflammatory disease which comprises administering to a mammal in need thereof an effective amount of the compounds of the present invention.

The present invention is also related to a method for the mediation or inhibition of the enzymatic or catalytic activity of PDE IV activity in mammals, particularly humans, which comprises administering an effective amount of the above-described compounds of the invention to a mammal in need of PDE IV inhibition.

The compounds of the present invention may find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

In certain preferred embodiments, the compounds of the present invention comprise the formula:

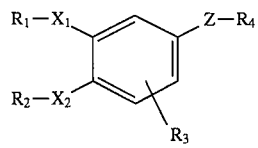

wherein:

$X_1$ and $X_2$ may be the same or different and each is O or S; and $R_1$ and $R_2$ may be the same or different and each is selected from the group consisting of hydrogen, saturated or unsaturated straight-chain or branched $C_{1-12}$ alkyl groups, cycloalkyl and cycloalkyl-alkyl groups containing from 3 to 10 carbon atoms in the cycloalkyl moiety;

$R_3$ is hydrogen, halogen, or a saturated or unsaturated straight-chain or branched $C_{1-12}$ alkyl group, a cycloalkyl and cycloalkyl-alkyl groups containing from 3 to 7 carbon atoms in the cycloalkyl moiety;

Z is a linkage selected from —NHCH$_2$—, —CH$_2$NH—, —CH$_2$CONH—, —CH$_2$NHCO—, —CH$_2$CO—, —COCH$_2$—, —CH$_2$COCH$_2$—, —C(=NQ)NH— and C(=NOCONHQ)—;

$R_4$ is a phenyl or benzyl or a 6-membered heteroaryl group which may be unsubstituted or substituted with one or more halogen atoms, alkyl groups, hydroxyl groups, cyano groups, nitro groups, carboxyl groups, alkoxy groups, alkoxycarbonyl, amido, carboxamido, substituted or unsubstituted amino groups, cycloalkyl and cycloalkyl-alkyl groups containing from 3 to 10 carbon atoms in the cycloalkyl moiety, aryl or aralkyl groups preferably containing from about 6 to about 10 carbon atoms, or heterocyclic groups containing nitrogen, oxygen or sulfur in the ring; said alkyl, cycloalkyl, cycloalkyl-alkyl, aryl, and aryl-alkyl groups being unsubstituted or substituted by halogen atoms, hydroxyl groups, cyano groups, carboxyl groups, alkoxy groups, alkoxycarbonyl, carboxamido or substituted or unsubstituted amino groups, or one or more lower alkyl groups having from 1 to 3 carbon atoms;

Q is $R_4$ or hydrogen;

except that when Z=—C(=NOCONHQ)—, $R_4$ is not benzyl; and $R_1$ and $R_2$ are both not hydrogen.

In certain preferred embodiments, $R_4$ is a phenyl or substituted phenyl having one of the structures:

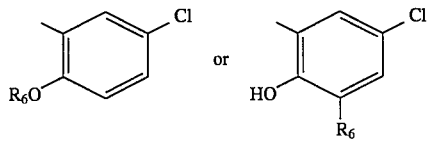

wherein $R_6$ is a substituted or unsubstituted lower alkyl having from about 1 to about 3 carbon atoms.

In another preferred embodiment $R_4$ is one of the following heteroaryl groups having the structure:

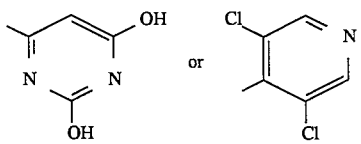

In further preferred embodiments, Z is a linkage NHCO—, —COCH$_2$—, —CH$_2$CO—, —C(=NQ)NH— and —C(=NOCONHQ)—.

Certain preferred compounds of the present invention include:

(I) N-(3-Cyclopentyloxy-4-methoxyphenyl-acetyl)-2-allyloxy-5-chloroaniline;

(II) N-(3-Cyclopentyloxy-4-methoxyphenyl-acetyl)-2-hydroxy-3-allyl-5-chloroaniline;

(III) 1-(3-Cyclopentyloxy-4-methoxyphenyl)phenone-O-(aminocarbonyl)oxime;

(IV) 1-(3-cyclopentyloxy-4-methoxyphenyl)-(2-(5-(pyrimid-2,4-dionyl)))ethanone; and (V) N-Benzyl-N'-(3,5-dichloropyrid-4-yl)-3-cyclopentyloxy-4-methoxybenzamidine.

Representative processes for preparing the compounds of the present invention are shown below:

Detailed description of several syntheses are shown in the Examples.

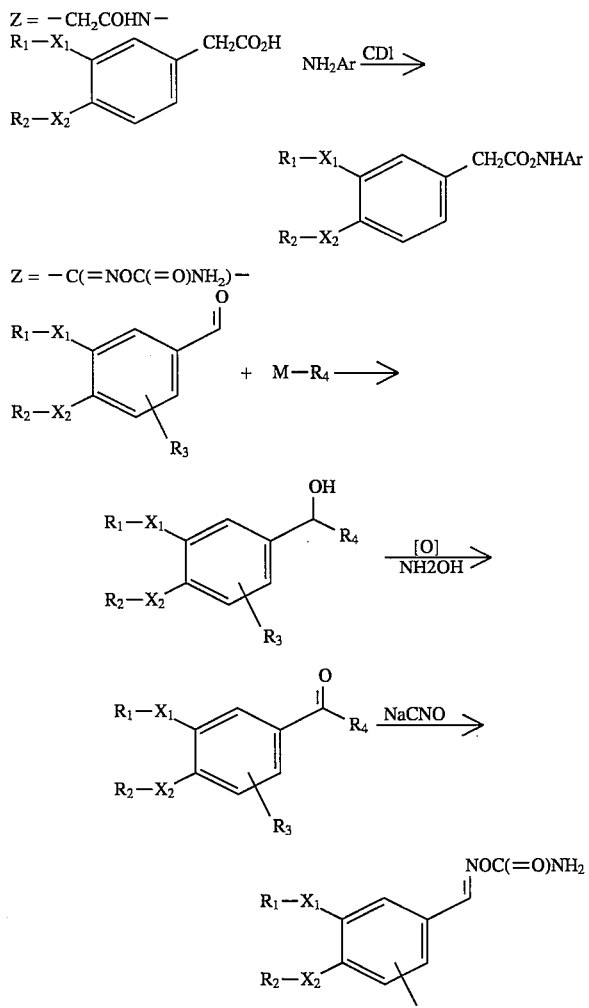

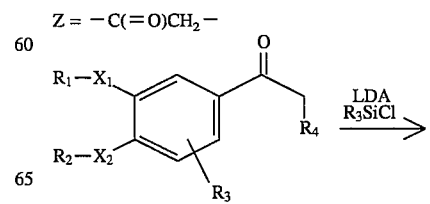

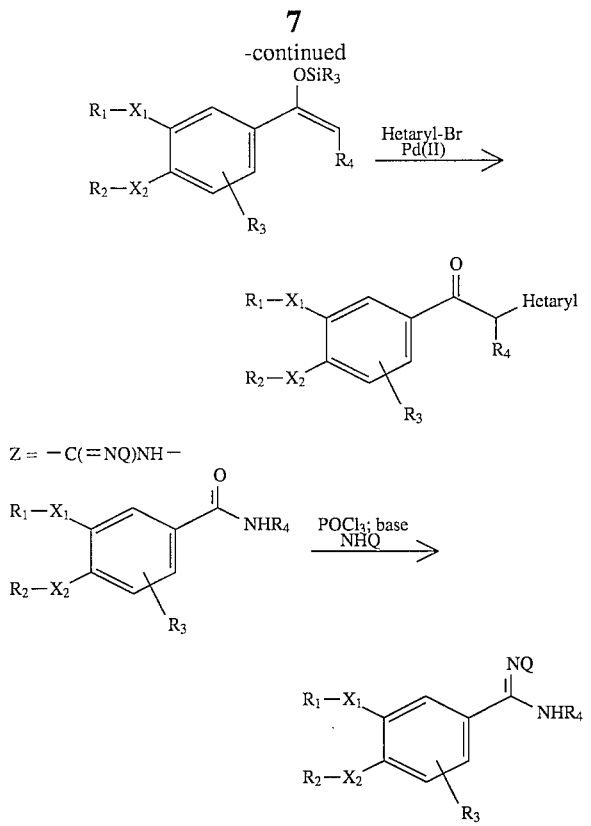

The compounds of the present invention have been found to be highly effective PDE IV inhibitors, the inhibition of which is in fact significantly and surprisingly greater than that of theophylline. The concentration which yields 50% inhibition of PDE IV ($IC_{50}$) for the compound prepared in Example 5 is 0.3 μM, whereas the $IC_{50}$ for rolipram when run in the same assay was 2.8 μM. It is apparent that this inventive compound is several times as effective as a PDE IV inhibitor as compared to rolipram (or theophylline).

Since the PDE III $IC_{50}$ of an Example 5 compound is >1000 uM, it is clear that the compound of the invention is highly selective as a PDE IV inhibitor.

Accordingly, the compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric*coated, sugar*coated, film*coated, multiply compressed or multiply layered. Liquid oral dosage forms include aqueous and nonaqueous solutions, emulsions, suspensions, and solutions and/or suspensions reconstituted from non*effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553*1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, sustained release agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The PDE IV inhibitory compounds of the present invention may be examined for their PDE IV inhibitory effects via the techniques set forth in the following examples, wherein the ability of the compounds to inhibit PDE IV isolated from bovine tracheal smooth muscle is set forth.

DESCRIPTION OF THE PREFERRED EMBODIMENTS

The following examples illustrate various aspects of the present invention, and are not to be construed to limit the claims in any manner whatsoever.

EXAMPLE 1

Preparation of
N-(3-Cyclopentyloxy-4-methoxyphenyl-acetyl)-2-allyloxy-5-chloroaniline a) 3-Cyclopentyloxy-4-methoxybenzyl alcohol A solution of 3-cyclopentyloxy-4-methoxybenzaldehyde (38 grams, 0.17 mol) in 40 milliliters of ethanol and sodium borohydride (1.63 grams, 0.043 mol) was stirred for 2 hours at room temperature until complete by TLC. The reaction was diluted with water and extracted with ethyl acetate. Evaporation of the ethyl acetate afforded 3-cyclopentyloxy-4-methoxybenzyl alcohol (37 grams, 98%) suitable for the next step.

b) 3-Cyclopentyloxy-4-methoxybenzyl chloride

A solution containing 3-cyclopentyloxy-4-methoxybenzyl alcohol (112 grams, 0.50 mol), prepared as described in step a), in 1 liter of methylene chloride was stirred at room temperature with concentrated HCl (110 milliliters, 1.2 mol) for 3 hours, at which time the reaction was done by TLC. The layers were separated and the methylene chloride solution was washed twice with water and evaporated under reduced pressure to give 3-cyclopentyloxy-4-methoxybenzyl chloride (119 grams, 100%).

c) 3-Cyclopentyloxy-4-methoxyphenylacetonitrile

A mixture of 3-cyclopentyloxy-4-methoxybenzyl chloride (119 grams, 0.49 mol), 120 milliliters of methylene chloride, KCN (70.7 grams, 1.09 mol), benzyltriethylammonium chloride (35 grams, 0.015 mol) and water (120 milliliters) was stirred vigorously at room temperature for 48 hours. The reaction mixture was diluted with methylene chloride and the layers were separated. The methylene chloride solution was extracted several times with water and evaporated to yield 3-cyclopentyloxy-4-methoxyphenylacetonitrile (109 grams, 95%) for the subsequent transformation.

d) 3-Cyclopentyloxy-4-methoxyphenylacetic acid

A solution of 3-cyclopentyloxy-4-methoxyphenylacetonitrile (109 grams, 0.43 mol) in 1330 milliliters of ethanol and NaOH (51 grams, 1.3 mol) was heated under reflux for 48 hours. Ethanol (500 milliliters) was distilled from the reaction mixture and the residue was diluted with water and stirred with Norit A (11 grams) for 2 minutes. The mixture was filtered through a pad of celite and acidified to pH 1 with concentrated HCl. Extraction of the mixture with diethyl ether yielded 120 grams of crude 3- cyclopentyloxy-4-methoxy-phenylacetic acid after evaporation of the ether at reduced pressure. The crude acid was dissolved in warm toluene (400 milliliters) and stirred for 1 hour with 10.5 grams of Norit A. The charcoal was filtered and the toluene solution was diluted with heptane (40 milliliters). Filtration of the cooled solution afforded 72 grams (67%) of pure 3-cyclopentyloxy-4-methoxyphenylacetic acid, mp 79°–80°.

e) N-(3-Cyclopentyloxy-4-methoxy-phenylacetyl)-2-hydroxy-5-chloroaniline

A solution of 3-cyclopentyloxy-4-methoxyphenylacetic acid (10 grams, 0.040 mol) in 20 milliliters of methylene chloride was added dropwise to a stirred slurry of 1,1'-carbonyldiimidazole (7.1 grams, 0.044 mol) in 40 milliliters of methylene chloride. After stirring for 2 hours, the resulting solution was added to a solution of 2-hydroxy-5-chloraniline (6.0 grams, 0.042 mol) in methylene chloride (75 milliliters). After stirring overnight, water was added and stirring was continued. The layers were separated and the methylene chloride layer was washed with 100 milliliter portions of water, dilute aqueous HCl, and water. Evaporation of the methylene chloride afforded the solid amide which was triturated with methanol (20 milliliter) and filtered to give 10.7 grams (71%) of N-(3-cyclopentyloxy-4-methoxyphenylacetyl)-2-hydroxy-5-chloraniline, mp 151°–152°.

f) N-(3-Cyclopentyloxy-4-methoxyphenyl-acetyl)-2-allyloxy-5-chloroaniline

In this step, allyl chloride (23.3 grams, 0.31 mol) was added to a stirred solution of N-(3-cyclopentyloxy-4-methoxyphenylacetyl)-2-hydroxy-5-chloroaniline (78 grams, 0.21 mol) in ethanol (600 milliliters) and 1N NaOH in methanol (213 millilters). The mixture was heated under reflux for 8 hours and then diluted with water and extracted twice with ethyl acetate. Evaporation of the ethyl acetate and crystallization of the residue from methanol gave 56.4 grams (65%) of the title compound, mp 75°–76.5°.

EXAMPLE 2

Preparation of
N-(3-Cyclopentyloxy-4-methoxyphenyl-acetyl)-2-hydroxy-3-allyl-5-chloroaniline A solution of N-(3-cyclopentyloxy-4-methoxyphenylacetyl)-2-allyloxy-5-chloroaniline (33 grams, 0.079 mol) in 330 milliliters of diphenyl ether was heated at 180° for 6.5 hours. This reaction mixture was combined with a second reaction mixture containing N-(3-cyclopentyloxy-4-methoxyphenylacetyl)-2-allyloxy-5-chloroaniline and 250 milliliters of diphenyl ether which had been heated at 180° for 20 hours.

The combined reaction mixtures were diluted with 800 milliliters of hexane and applied to a flash chromatography column prepared from 470 grams of flash chromatography silica gel. Fractions of 800 milliliters were collected. Fractions 1–6 (hexane) contained only diphenyl ether. Fraction 7 (1:1 hexane/methylene chloride) contained 1 gram of material. Fractions 8–11 (methylene chloride) contained 34.5 grams of material with a higher $R_f$ on TLC (2% methanol/methylene chloride, silica gel) than the title compound. Fractions 12–17 (methylene chloride) gave 20 grams (34%) of the crude title compound. A sample of this material (1.0 grams) was recrystallized from 10 milliliters of ethanol to give the pure title compound, mp 119°–120°.

EXAMPLE 3

Preparation of 1-(3-Cyclopentyloxy-4-methoxyphenyl)phenone-O-(aminocarbonyl)oxime a) α-Phenyl-3-cyclopentyloxy-4-methoxybenzyl alcohol Phenyllithium (1.8M solution in cyclohexane/diethyl ether, 25.5 milliliters, 46 mmol) was added dropwise over 15 minutes to a stirred solution of 3-cyclopentyloxy-4-methoxybenz-aldehyde (6 grams, 27 mmol) in dry tetrahydrofuran (20 milliliters) at −78° C. The resulting solution was stirred at −78° C. for 30 minutes and quenched at −78° C. by the rapid addition of aqueous saturated $NH_4Cl$ (70 milliliters). After warming to room temperature, water was added to dissolve the solids and volatiles were removed in vacuo. The residue was partitioned between water (250 milliliters)

and ethyl acetate (250 milliliters), the aqueous phase was extracted with ethyl acetate (3×250 milliliters) and the combined organic layers washed with water (200 milliliters). The organics were dried over $Na_2SO_4$ and concentrated in vacuo to give a light yellow oil. The oil was purified by flash chromatography ($SiO_2$:hexane/ethyl acetate (4:1)) to afford the title compound as a pale yellow oil (7.4 grams)

$^1$H NMR ($CDCl_3$,250 MHz) δ 7.30 (m, 5H), 6.84 (m,3H), 5.76 (s, 1H), 4.72 (m, 1H), 3.81 (s, 3H), 2.26 (s, 1S), 1.85 (m, 6H), 1.59 (m, 2H).

b) 1-(3-Cyclopentyloxy-4-methoxyphenyl)phenone

Pyridinium dichromate (13.22 grams, 35.19 mmol) was added in one portion to a stirred solution of α-phenyl-3-cyclopentyloxy-4-methoxybenzyl alcohol (7.0 grams, 23.5 mmol) in dry methylene chloride (200 milliliters) at room temperature. The resulting heterogeneous solution was stirred at room temperature overnight. The reaction mixture was diluted with an equal volume of diethyl ether and stirred for 1 hour. The mixture was filtered through celite and the filter cake washed with diethyl ether (150 milliliters) and ethyl acetate (150 milliliters). The brown filtrate was concentrated in vacuo and purified by flash chromatography ($SiO_2$:hexane/ethyl acetate (7:3) to yield the title compound as an orange solid (6.940 grams).

$^1$H NMR ($CDCl_3$,250 MHz) δ 7.75 (m, 2H), 7.46 (m,5H), 5.76 (s, 1H), 4.72 (m, 1H), 3.81 (s, 3H), 2.26 (s, 1H), 1.85 (m, 6H), 1.59 (m, 2H).

c) 1-(3-Cyclopentyloxy-4-methoxyphenyl)phenone oxime

Hydroxylamine hydrochloride (1.179 grams, 25.7 mmol) was added in one portion to a magnetically stirred solution of 1-(3-cyclopentyloxy-4-methoxyphenyl)phenone (6.936 grams, 23.4 mmol) in dry pyridine (120 milliliters) at room temperature. The resulting suspension slowly became homogeneous and the solution was stirred at room temperature overnight. Further hydroxylamine hydrochloride (0.5 grams, 7.17 mmol) was added to the reaction mixture and stirring continued overnight. The pyridine was removed in vacuo and the residue partitioned between ethyl acetate (200 milliliters) and water (200 milliliters). The aqueous phase was extracted with ethyl acetate (2×125 milliliters), the organics dried over $Na_2SO_4$ and concentrated in vacuo to give an orange oil. The oil was purified by flash chromatography ($SiO_2$:hexane/ethyl acetate (4:1)) to afford the title compound as a tan solid (2.49 grams).

$R_f$ ($SiO_2$:ethyl acetate/hexane (3:7)) 0.25.

d) 1-(3-Cyclopentyloxy-4-methoxy-phenyl)phenone-O-(aminocarbonyl)oxime

Anhydrous trifluoroacetic acid (2.45 milliliters, 3.64 grams, 31.92 mmol) was addded dropwise over 10 minutes at room temperature to a slowly stirred suspension of sodium cyanate (4.15 grams, 63.84 mmol) in methylene chloride (30 milliliters). The suspension slowly thickened to a gelatinous mass which was periodically agitated by hand. After 30 minutes at room temperature, 1-(3-cyclopentyloxy-4-methoxyphenyl)phenone oxime (2.49 grams, 7.99 mmol) in methylene chloride (10 milliliters) was added in one portion and the reaction mixture stirred under nitrogen for 1 hour. The reaction mixture was poured into saturated $NaHCO_3$ (100 milliliters) and extracted with methylene chloride (2×200 milliliters). The organic phase was washed with water (100 milliliters), dried ($Na_2SO_4$) and concentrated in vacuo to give a pale yellow oil. The oil was purified by flash chromatography ($SiO_2$:methylene chloride/ethyl acetate (9:1)) to yield the title compound as a white solid (1.21 grams). m.p. 129°–132° C.

$^1$H NMR ($CDCl_3$,250 MHz) δ 7.43 (m, 5H), 6.94 (m,3H), 4.69 (m, 1H), 3.86 (3, 3H), 1.78 (m, 6H), 1.60 (m, 2H).

EXAMPLE 4

Preparation of 1-(3-cyclopentyloxy-4-methoxyphenyl)-(2-(5-(pyrimid-2,4-dionyl)))ethanone a) [[1-(3-Cyclopentyloxy-4-methoxyphenyl)-1-ethenyl]oxy]trimethylsilane Lithium diisopropylamide (1.5M solution in cyclohexane, 12.5 milliliters, 18.75 mmol) was added over 3 minutes to a stirred solution of 3-cyclopentyloxy-4-methoxyacetophenone (3 grams, 12.8 mmol) in dry tetrahydrofuran (10 milliliters) at −78° C. After the addition was complete, the solution was stirred for 30 minutes at −78° C. and trimethylsilyl chloride (2.4 milliliters, 30.72 mmol) was added in one portion. The mixture was allowed to warm to room temperature, stirred for 20 minutes, and quenched with saturated $NaHCO_3$ (35 milliliters). The resulting mixture was extracted with hexane (2×50 milliliters), the organic layer dried ($Na_2SO_4$) and the solvent removed in vacuo to afford the title compound as a colorless oil (4 grams); 80% pure by gas chromatography/mass spectrometry.

b) 1-(3-cyclopentyloxy-4-methoxyphenyl)-(2-(5-(pyrimid-2,4-dionyl)))ethanone

A stirred solution of ([1-(3-cyclopentyloxy-4-methoxyphenyl)-1-ethenyl)oxy]trimethylsilane (4.0 grams, 80% pure by gas chromatography, 10.3 mmol), 5-bromouracil (1.73 grams, 9.14 mmol), tributyltin fluoride (2.8 grams, 9.14 mmol) and bis(triphenylphosphine)palladium (II) chloride (215 milligrams, $3.0×10^{-4}$ mmol) in 1,4 dioxane (50 milliliters) was refluxed for 60 hours. The reaction mixture was cooled to room temperature, diluted with diethyl ether (150 milliliters) and washed with 1N NaOH (3×60 milliliters). The aqueous layer was neutralized with 12N HCl and extracted with methylene chloride (3×50 milliliters). The organics were dried ($Na_2SO_4$) and the solvent removed in vacuo to afford an oil. The oil was purified by chromatography on $SiO_2$ eluting with methylene chloride/ethanol/ammonia (9:1:0.1) to yield the title compound as a white solid (70 milligrams).

$^1$H NMR ($CDCl_3$;250 MHz) δ 9.28 (brs, 1H), 8.87 (brs, 1H), 7.16 (s, 1H), 6.84 (m, 3H), 5.69 (s, 1H), 5.46 (s, 1H), 4.75 (m, 1H), 3.83 (s, 3H), 1.81 (m, 6H), 1.57 (m, 2H).

EXAMPLE 5

N-Benzyl-N'-(3,5-dichloropyrid-4-yl)-3-cyclopentyloxy-4-methoxybenzamidine

A solution of N-(3,5-dichloropyrid-4-yl)-3-cyclopentyloxy-4-methoxybenzamide (1 gram, 2.62 mmol) in phosphoryl chloride (15 milliliters, 161 mmol) and N, N-dimethylaniline (0.75 milliliters) was refluxed under nitrogen for 20 hours. The mixture was cooled to room temperature, volatiles removed in-vacuo, and the brown residue azeotroped with toluene (3×20 milliliters). The crude imino chloride was dissolved in toluene (15 milliliters), an excess of benzylamine (2.57 milliliters, 23.58 mmol) was added in one portion and the mixture refluxed, under nitrogen, for 4 hours. The mixture was cooled to room temperature, volatiles removed in-vacuo, and the residue dissolved in chloroform ( 100 milliliters) and washed with water (2×50 milliliters). The combined organics were dried ($Na_2SO_4$) and volatiles removed in-vacuo to yield a white solid. The mixture was purified by flash chromatography ($SiO_2$; ethyl acetate: hexane (1:9), followed by ethyl acetate: hexane (1:4)) to yield the title compound (624 milligrams, 50 %) as a white crystalline solid, m.p. 129°–133° C.

$\delta_H$ (250 MHz; CDCl$_3$) 1.63 (8H, m, 4×CH$_2$), 3.78 (3H, s, OMe), 4.46 (1H, m, CH), 4.74 (2H, d, ArCH$_2$), 5.38 (1H, t, NH), 6.71 (2H, m, 2×ArH), 6.95 (1H, dd, ArH), 7.38 (5H, m, 5×ArH), 8.20 (2H, s, 2×ArH).

EXAMPLE 6

Protocols for PDE III and PDE IV inhibition activity are set forth below:

Type III Phosphodiesterase

Enzyme Isolation Protocol

The Type III PDE is isolated from human platelets using a procedure similar to that previously described by Weishaar, R. E., et al., Biochem. Pharmacol., 35:787, 1986. Briefly, 1–2 units of platelets are suspended in an equal volume of buffer (20 mM Tris-HCl, pH 7.5, containing 2 mM magnesium acetate, 1 mM dithiothreitol, and 5 mM Na$_2$ EDTA). The proteinase inhibitor phenylmethyl-sulfonyl fluoride (PMSF) is also included in this buffer at a final concentration of 200 μM. The suspension is homogenized using a polytron and the homogenate centrifuged at 100,000×g for 60 minutes. This and all subsequent procedures are performed at 0°–4° C. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200 μM PMSF). After application of the sample, the column is washed with several bed volumes of buffer B, after which the different forms of PDE are eluted from the column using two successive linear NaCl gradients (0.05–0.15M, 300 milliliters total; 0.15–0.40M, 200 milliliters total). Five milliliter fractions are collected and assayed for cyclic AMP and cyclic GMP PDE activity. Fractions containing PDE III activity are pooled and dialyzed overnight against 4 liters of buffer B. The dialyzed PDE III is then concentrated to 10% of the original volume, diluted to 50% with ethylene glycol monoethyl ether and stored at −20° C. PDE III can typically be retained for up to four weeks with little or no loss of activity.

Measuring Type III PDE Activity

Enzyme activity is assessed by measuring the hydrolysis of [$^3$H]-cyclic AMP, as described by Thompson, W. J., et al., Adv. Cyclic Nucleotide Res. 10:69, 1979. The cyclic AMP concentration used in this assay is 0.2 μM, which approximates to the K$_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase

Enzyme Isolation Protocol

The Type IV PDE is isolated from bovine tracheal smooth muscle using a procedure similar to that previously described by Silver, P. J., et al. Eur. J. Pharmacol. 150:85, 1988. Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/milliliters of aprotinin. This and all subsequent procedures are performed at 0°–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity

Enzyme activity is assessed by measuring the hydrolysis of [$^3$H]-cyclic AMP, as described by Thompson, W. J., et al., Adv. Cyclic Nucleotide Res. 10:69, 1979. The cyclic AMP concentration used in this assay is 0.2 μM, which approximates the K$_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

EXAMPLE 7

Following the above procedures, the PDE III and PDE IV inhibition for the compounds of Examples 1–5, and rolipram were tested and compared. The results are shown in the Table below:

TABLE

| | IC$_{50}$ (μM) | |
| --- | --- | --- |
| Compound | PDE III ACTIVITY | PDE IV ACTIVITY |
| Example 1 | >1000 | 2.2 |
| Example 2 | >1000 | 2.8 |
| Example 3 | 89.5 | 1.8 |
| Example 4 | 205.4 | 3.2 |
| Example 5 | >1000 | 0.3 |
| Rolipram | 790 | 2.8 |

Thus, it can be seen from the foregoing that compounds prepared in accordance with the present invention have high levels of PDE IV inhibition while, at the same time relatively low levels of PDE III inhibition.

While the invention has been illustrated with respect to the production and use of a particular compound, it is apparent that variations and modifications of the invention can be made without departing from the spirit or scope of the invention.

What is claimed is:

1. A compound of the formula:

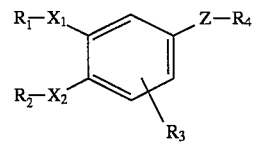

wherein:

X$_1$ and X$_2$ may be the same or different and each is O or S;

$R_1$ is selected from the group consisting of cycloalkyl and cycloalkyl-alkyl groups containing from 3 to 10 carbon atoms in the cycloalkyl moiety;

$R_2$ is $R_1$ or $CH_3$;

$R_3$ is hydrogen, halogen, or a saturated or unsaturated straight-chain or branched $C_{1-12}$ alkyl group, a cycloalkyl or cycloalkyl-alkyl groups containing from 3 to 7 carbon atoms in the cycloalkyl moiety;

Z is a linkage selected from —$CH_2CONH$— and —$CH_2NHCO$—; and $R_4$ is a phenyl or benzyl which may be unsubstituted or substituted with one or more halogen atoms, alkyl groups, hydroxyl groups, cyano groups, carboxyl groups, alkoxy groups, alkoxycarbonyl, amido, carboxamido, substituted or unsubstituted amino groups, cycloalkyl and cycloalkyl-alkyl groups containing from 3 to 10 carbon atoms in the cycloalkyl moiety, aryl or aralkyl groups preferably containing from about 6 to about 10 carbon atoms, or heterocyclic groups containing nitrogen, oxygen or sulfur in the ring; said alkyl, alkoxy, cycloalkyl, cycloalkyl-alkyl, aryl, and arylalkyl groups being saturated or unsaturated, unsubstituted or substituted by halogen atoms, hydroxyl groups, cyano groups, carboxyl groups, alkoxy groups, alkoxycarbonyl, carboxamido or substituted or unsubstituted amino groups, or one or more lower alkyl groups having from 1 to 3 carbon atoms;

provided that $R_4$ cannot be substituted with more than one methoxy group.

2. The compound of claim 1, wherein $R_1$ is a cycloalkyl of 3–6 carbon atoms, said cycloalkyl may be substituted by one or more alkyl groups or by one or more halogens, $R_2$ is hydrogen, or $C_{1-12}$ alkyl, and wherein $R_3$ is hydrogen, lower alkyl or halogen.

3. The compound of claim 2 wherein $R_1$ is cycloalkyl optionally substituted by one or more halogens.

4. The compound of claim 1 wherein $R_2$ is methyl or and wherein $R_1$ is cyclopentyl optionally substituted by $R_5$ as shown in the following structural formula:

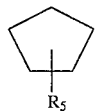

wherein $R_5$ is hydrogen or a saturated or unsaturated straight-chain lower alkyl group containing from about 1 to about 6 carbon atoms, unsubstituted or substituted with one or more halogen atoms, hydroxyl groups, cyano groups, nitro groups, carboxyl groups, alkoxy groups, alkoxycarbonyl, carboxamido or substituted or unsubstituted amino groups.

5. The compound of claim 2 wherein Z is a linkage selected from the group consisting of —$CH_2CONH$—, —$CH_2NHCO$—.

6. The compound of claim 2, wherein $X_1$ and $X_2$ are O.

7. The compound of claim 2 wherein $R_4$ is an unsubstituted or substituted phenyl or benzyl.

8. The compound of claim 6 wherein $R_4$ is a substituted phenyl having one of the following structures:

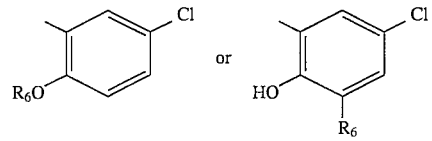

wherein $R_6$ is an unsubstituted or substituted lower alkyl.

9. The compound of claim 1, selected from the group consisting of:

N-(3-Cyclopentyloxy-4-methoxyphenyl-acetyl)-2-allyloxy-5-chloroaniline; and N-(3-Cyclopentyloxy-4-methoxyphenyl-acetyl)-2-hydroxy-3-allyl-5-chloroaniline.

10. A method of effecting selective PDE IV inhibition to a patient requiring the same, comprising administering an effective amount of the compound of claim 1.

11. The method of claim 10, wherein said compound is selected from the group consisting of:

N-(3-Cyclopentyloxy-4-methoxyphenyl-acetyl)-2-allyloxy-5-chloroaniline; and N-(3-Cyclopentyloxy-4-methoxyphenyl-acetyl)-2-hydroxy-3-allyl-5-chloroaniline.

12. A pharmaceutical composition comprising the compound of claim 1.

13. The pharmaceutical composition of claim 12, wherein said compound is selected from the group consisting of:

N-(3-Cyclopentyloxy-4-methoxyphenyl-acetyl)-2-allyloxy-5-chloroaniline; and N-(3-Cyclopentyloxy-4-methoxyphenyl-acetyl)-2-hydroxy-3-allyl-5-chloroaniline.

14. A method of treating a mammal suffering from a disease state selected from the group consisting of asthma, allergies, inflammation, depression, dementia, atopic diseases, rhinitis and disease states associated with abnormally high physiological levels of cytokine, comprising administering an effective amount of the compound of claim 1.

15. The method of claim 14, wherein said compound is selected from the group consisting of:

N-(3 -Cyclopentyloxy-4-methoxyphenyl-acetyl)-2-allyloxy-5-chloroaniline; and N-(3-Cyclopentyloxy-4-methoxyphenyl-acetyl)-2-hydroxy-3-allyl-5-chloroaniline.

* * * * *